United States Patent
Beck

(10) Patent No.: US 8,647,266 B2
(45) Date of Patent: Feb. 11, 2014

(54) SPECULUM

(75) Inventor: C. Joseph Beck, Wichita, KS (US)

(73) Assignee: THB Precision, LLC, Wichita, KS (US)

( * ) Notice: Subject to any disclaimer, the term of this patent is extended or adjusted under 35 U.S.C. 154(b) by 27 days.

(21) Appl. No.: 13/277,009

(22) Filed: Oct. 19, 2011

(65) Prior Publication Data

US 2012/0071726 A1 Mar. 22, 2012

Related U.S. Application Data

(63) Continuation-in-part of application No. 12/042,803, filed on Mar. 5, 2008, now Pat. No. 8,066,635.

(51) Int. Cl.
*A61B 1/32* (2006.01)
(52) U.S. Cl.
USPC ........... 600/236; 600/217; 600/218; 600/226; 600/235
(58) Field of Classification Search
USPC ......... 600/206, 208, 210, 213, 214, 217, 218, 600/226, 235, 236, 242; 403/252, 254, 360
See application file for complete search history.

(56) References Cited

U.S. PATENT DOCUMENTS

| | | | | |
|---|---|---|---|---|
| 362,548 A | * | 5/1887 | Smith | 411/513 |
| 2,702,540 A | * | 2/1955 | Debeh | 600/218 |
| 3,132,887 A | * | 5/1964 | Martinez | 294/1.2 |
| 3,680,546 A | * | 8/1972 | Asrican | 600/219 |
| 5,070,860 A | * | 12/1991 | Grounauer | 600/236 |
| 6,440,065 B1 | * | 8/2002 | Hered | 600/236 |
| 2003/0216737 A1 | * | 11/2003 | Biscup | 606/61 |

FOREIGN PATENT DOCUMENTS

DE 4322602 A1 * 2/1994 ............ A61B 17/28

OTHER PUBLICATIONS

Translation of DE 4322602 A1 to English. Accessed from the European Patent Office at epo.org on Apr. 23, 2013.*

* cited by examiner

*Primary Examiner* — Eduardo C. Robert
*Assistant Examiner* — Julianna N Harvey
(74) *Attorney, Agent, or Firm* — Standley Law Group LLP

(57) ABSTRACT

A speculum having first and second arms beginning at a proximal point and ending at a distal end and having a cup positioned at the distal end, an attachment portion positioned on the first arm and proximal to the cup, and a user manipulation element positioned within the attachment portion. In another embodiment the speculum has a generally U-shaped frame having a proximal point and pair of distal ends, a pair of cups attached to the distal ends, a pair of user manipulation elements attached to the frame and positioned between the cups and the proximal point so that the user manipulation elements can rotate relative to the frame.

20 Claims, 3 Drawing Sheets

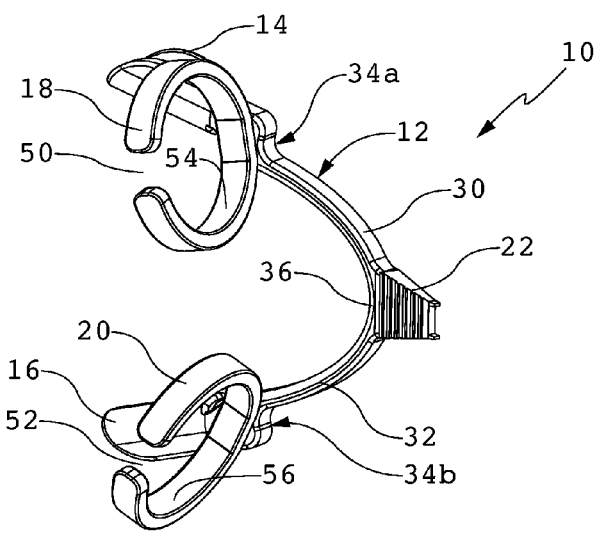
FIG. 1
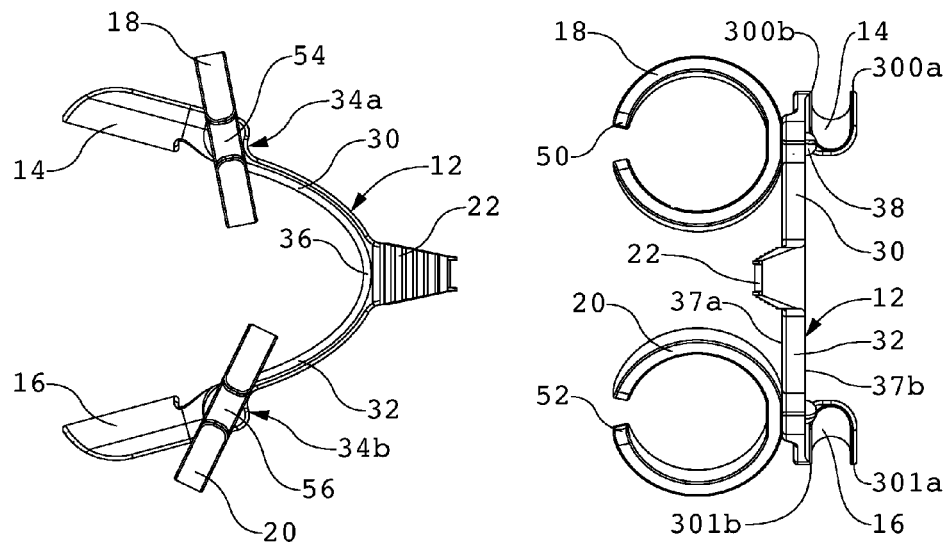
FIG. 2  FIG. 3

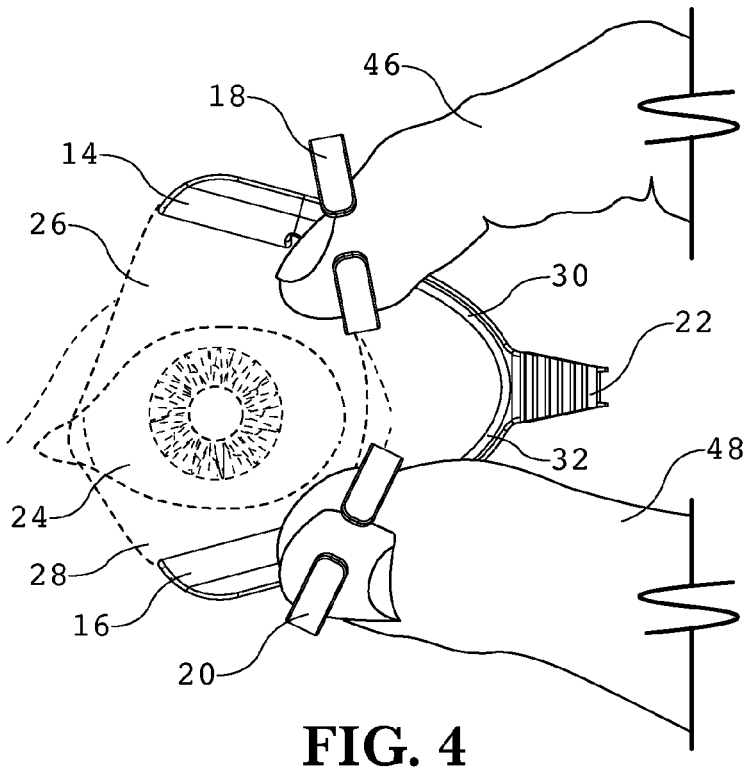
FIG. 4
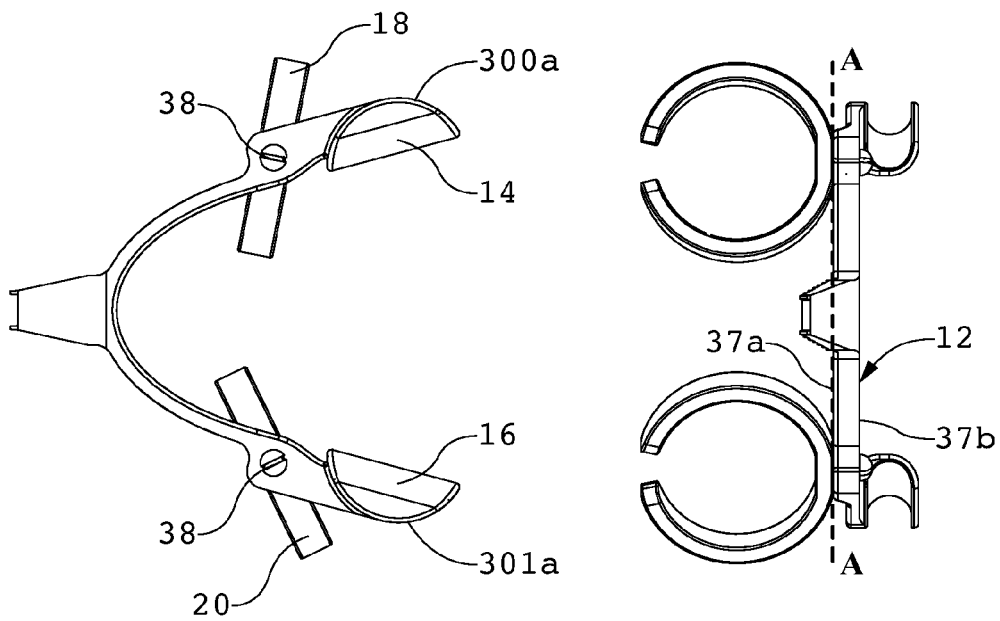
FIG. 5
FIG. 6

SPECULUM

CROSS-REFERENCE TO RELATED APPLICATIONS

This application is a continuation-in-part of co-pending U.S. application Ser. No. 12/042,803 filed on Mar. 5, 2008 and is herein incorporated by reference in its entirety.

BACKGROUND

1. Technical Field

The exemplary embodiments of the present invention relate generally to a speculum, and more particularly to a speculum for retracting the marginal edge portions of a body cavity or opening and providing enhanced access to the retracted area.

2. Background of the Art

A speculum retracts the marginal edge portions of a body cavity or opening to dilate the opening and provide enhanced access to the underlying anatomic structures. An eyelid speculum retracts the upper and lower eyelids surrounding an eyeball to provide access to the eyeball for examination or performance of a surgical procedure.

One type of eyelid speculum is formed from a loop of wire and has an upper portion that engages an upper eyelid and a lower portion that engages a lower eyelid. The upper and lower portions spread apart to retract the eyelids and expose the eyeball. Because this type of speculum is formed from a loop of wire it only applies force to a small area of each upper and lower eyelid, thus increasing the potential for injury to the eyelids. This type of speculum also does not prevent the eyelashes from contacting the exposed portion of the eyeball, which is a well known cause of infection during eye surgery. The wire loop speculum retracts the midportion of the eyelids for access to the cornea and anterior chamber of the eyeball. The speculum does not retract the eyelids along the temporal or nasal side of the eye cavity. When injecting a pharmaceutical into an eyeball, it is desirable to inject the pharmaceutical into the inferotemporal region of the pars plana in order to avoid damage to the lens or retina. To insert the needle into the inferotemporal region of the pars plana, the temporal side of the lower eyelid must be retracted. A conventional wire loop eyelid speculum does not retract the temporal side of the lower eyelid for injecting a pharmaceutical into the inferotemporal region of the pars plana.

BRIEF SUMMARY OF THE EXEMPLARY EMBODIMENTS

One exemplary embodiment of the present invention comprises a first arm beginning at a proximal point and ending at a distal end and having: a cup positioned at the distal end; an attachment portion positioned proximal to the cup; and a user manipulation element positioned within the attachment portion; and a second arm extending from the proximal point of the first arm to comprise a substantial mirror image of the first arm. The user manipulation elements can be rings which are adapted to receive the finder of a user or simply a pair of rectangular projections. Preferably, the speculum exposes a desired portion of an eyeball by positioning each cup around corresponding portions of an upper or lower eyelid and manipulating the user manipulation elements to retract the eyelids, however, the speculum may be used to dilate any opening.

Another exemplary embodiment of the present invention comprises a generally U-shaped frame having a proximal point and pair of distal ends; a first cup attached to one of the distal ends; a second cup attached to the remaining distal end; a first user manipulation element attached to the frame and positioned between the first cup and the proximal point so that the user manipulation element can rotate relative to the frame; and a second user manipulation element attached to the frame and positioned between the second cup and the proximal point so that the user manipulation element can rotate relative to the frame.

The preferred mode of operating the speculum according to the present invention comprises squeezing the user manipulation elements together to reduce the distance between the cups and positioning one of the cups around an upper eyelid and the other cup around a lower eyelid (or other body opening). The user manipulation elements may then be released and/or receive a force applied thereto to increase the distance between the cups and the upper and lower eyelids and expose a desired portion of the eyeball. Preferably, the distance between the cups and position of the cups corresponds with a desirable location between the upper and lower eyelids for performing a surgical procedure on the eyeball. The arms or frame are also preferably made from an elastic material so they can be pushed outwardly to further increase the distance between the cups and expose more of the eyeball. In addition, the arms can be manipulated independent of one another such that the lower arm, for example, can be forced to further retract and expose a larger portion of the eyeball while maintaining the upper arm in a fixed position.

Additional aspects of the invention, together with the advantages and novel features appurtenant thereto, will be set forth in part in the description which follows, and in part will become apparent to those skilled in the art upon examination of the following, or may be learned from the practice of the invention. The objects and advantages of the invention may be realized and attained by means of the instrumentalities and combinations particularly pointed out in the appended claims.

BRIEF DESCRIPTION OF THE DRAWINGS

FIG. 1 is a perspective view of a speculum according to one embodiment of the present invention;

FIG. 2 is a top plan view of the speculum of FIG. 1;

FIG. 3 is a side elevational view of the speculum of FIG. 1;

FIG. 4 is a top plan view of the speculum of FIG. 1 used to retract upper and lower eyelids;

FIG. 5 is a bottom plan view of the speculum of FIG. 1;

FIG. 6 is a side elevational view of the speculum of FIG. 1, showing line A-A representing an imaginary plane in which the top surface of speculum extends;

DETAILED DESCRIPTION OF PREFERRED EMBODIMENT

Figure 7:
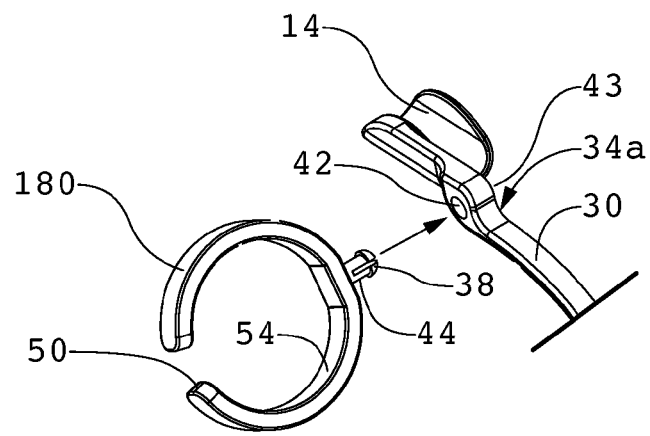
FIG. 7 is a fragmentary exploded perspective view of the speculum of FIG. 1.

Referring now to FIG. 1, a speculum in accordance with one embodiment of the present invention is indicated generally as 10. The speculum has a generally U-shaped frame 12, first and second cups 14 and 16 rigidly joined with the frame, first and second user manipulation elements 18 and 20 removably joined with first and second cups 14 and 16 and extending upward from frame 12, and a tab 22 rigidly joined with frame 12. As shown in FIG. 4, the speculum exposes a desired portion of an eyeball 24 by retracting the upper and lower eyelids 26 and 28 surrounding the eyeball. Although speculum 10 is shown retracting upper and lower eyelids, the speculum may be used to retract the marginal edges surrounding any body cavity or opening. Additionally, the speculum may either be disposable or reusable after sterilization.

Referring now to FIGS. 1-3, U-shaped frame 12 has first and second arms 30 and 32. Arms 30 and 32 have distal ends 34a and 34b, respectively, and are joined at proximal point 36. As shown in FIG. 3, frame 12 has a top 37a and a bottom 37b that is adjacent eyeball 24 when the speculum is in use (shown in FIG. 4). The top 37a of frame 12 is positioned in a primary speculum plane, which is represented by the line A-A in FIG. 6. The distance between distal ends 34a and 34b preferably ranges between 30 to 40 millimeters and is most preferably about 35 millimeters, although it is within the scope of the invention for the distance between the ends to be any length. The distance between each of distal ends 34a and 34b and proximal point 36 preferably ranges between 20 to 30 millimeters and is most preferably about 25 millimeters, although it is within the scope of the invention for this distance to be any length. Frame 12 preferably has a square cross section with a length and width of approximately two millimeters. Although frame 12 is shown with a square cross section, the cross section of the frame may be any shape. For example, frame 12 may have a circular, triangular, rectangular or trapezoidal cross section. Frame 12 is preferably made from an elastic material such that arms 30 and 32 return to their original shape when no pressure is applied to the arms. Preferably, each arm 30 and 32 may be moved independently such that when the speculum is in use one side of an opening may be retracted farther than the other. The frame is preferably constructed from a plastic inert material such as polyethylene, polypropylene, polyvinylchloride, acrylic butadiene styrene, nylon, polystyrene or polyurethane, but the frame may be constructed from any material including steel, stainless steel, aluminum or titanium.

First and second cups 14 and 16 are preferably attached to the distal ends 34a, 34b of arms 30 and 32, respectively. The first and second cups may be formed integrally with frame 12 or they may be joined to the frame with fasteners, adhesive, or by a thermal bonding technique such as brazing, soldering, or oxyfuel gas, resistance, electric arc, hot wire, hot gas or infrared welding. Each cup 14 and 16 has a generally U-shaped cross-section when viewed in a plane that is substantially perpendicular to the arms. As shown in FIGS. 3 and 5, the U-shape of the cups may be described as having an inside edge 300a and 301a which is adapted to fit underneath the marginal edge of the cavity to be dilated, in this example it would be underneath the eyelid. The cups may also contain an outside edge 300b and 301b which opposes the inside edge 300a and 301a. The spacing between the inside and outside edges of the cup is preferably selected to provide maximum control over the marginal edges of the cavity to be dilated. When used in a procedure with the eye, the spacing should be selected to provide maximum coverage and control of the eye lashes. As shown in FIG. 5, the inside edges 300a and 301a preferably have a profile that is a continuous arc. This has been found to minimize pressure on the inner aspect of the eyelid (palpebral conjunctiva). One cup may be rotated towards the lateral canthus.

For each cup, the distance or gap between the two "legs" of the U preferably corresponds with a desirable distance for receiving an upper or lower eyelid as shown in FIG. 4. For an adult person this distance is preferably between three to five millimeters. The dimensions of each cup when viewed from the top, as shown in FIGS. 2 and 4, are preferably sized to contain the eyelashes on the upper and lower eyelids when in use, thus preventing the eyelashes from contacting the eyeball in the region exposed by the speculum. It should be understood that the preferable cup dimensions disclosed above are not essential to the invention and that the cups may have any dimensions. For example, the cups are preferably smaller for retracting the eyelids of children. The cups may also be sized such that they are configured to retract the marginal edge portions of other body cavities or openings. The cups are preferably made from the same material as the frame, but it is within the scope of the invention for the cups to be made from a different material than the frame.

Referring now to FIGS. 1-4, each user manipulation element 18 and 20 extends upward from the top 37a of frame 12 such that the ring is configured to receive a force in a direction that is outside of the primary speculum plane represented by the line A-A in FIG. 6. In this manner, a user can freely access and manipulate the speculum via the user manipulation elements in a position above and remote from the eye area. In an exemplary embodiment, the user manipulation elements 18 and 20 may comprise a ring or other annular surface, preferably having an interior diameter which is slightly larger than an index finger 46 and a thumb 48, respectively. Preferably, the interior diameter of each ring is between 15 to 25 millimeters and most preferably the diameter is about 20 millimeters. The rings 18 and 20 may also have a gap 50 and 52, respectively, at the top of the ring so that the ring is expandable to accommodate a larger finger or thumb. Each ring may have an interior surface 54 and 56, respectively, which is generally annular except for the respective gap 50, 52. A majority of each annular surface 54 and 56 may extend upward at an angle from arms 30 and 32.

As shown in FIG. 4, finger 46 is in contact with the interior surface of user manipulation element 18 and thumb 48 is in contact with the interior surface of user manipulation element 20. Finger 46 and thumb 48 are in contact with surfaces 54 and 56 (shown in FIG. 1) for manipulating the position of cups 14 and 16. Surfaces 54 and 56 may be squeezed toward each other to reduce the distance between cups 14 and 16. Surfaces 54 and 56 may also be spread apart to increase the distance between cups 14 and 16. Finger 46 and thumb 48 may also move the entire frame 12 by applying a force to the respective surface 54 and 56.

Although surfaces 54 and 56 are generally annular, it is within the scope of the invention for the surfaces to have any shape. For instance, the surfaces could be rectangular or trapezoidal. Although user manipulation elements 18 and 20, and their respective surfaces 54 and 56, are shown removably joined with cups 14 and 16, it is within the scope of the invention for the user manipulation elements to be either removably or rigidly joined with either the arms or the cups. Each user manipulation element is preferably made from the same material as frame 12, however, it is within the scope of the invention for the user manipulation element to be made from a different material.

FIG. 7 illustrates an embodiment using a ring 180 which is configured to be rotationally and removably joined with the arm 30 via a compressible prong 44 which is received by an opening 42 in the attachment portion 43. Compressible prong 44 preferably has a retaining ledge 38 having a diameter that is slightly larger than opening 42 so the compressible prong 44 is retained within the attachment portion 43 after it is pressed through the opening 42. Compressible prong 44 preferably has a diameter which is slightly smaller than the diameter of the opening 42 such that the compressible prong can rotate with respect to the arm 30 and cup 14. There may also be more than one attachment portion 43 for positioning the ring 180 at different locations on the arm 30.

Referring now to FIGS. 1-3, an optional tab 22 extends outwardly from frame 12 adjacent proximal point 36. It should be noted that although shown extending upward from the top 37a of the frame 12, the tab 22 may extend upward or downward at an angle from the top 37a of frame 12. The angle from the top 37a of frame 12 may be chosen to minimize interference with instrumentation from a temporal approach and/or draping. The tab 22 may be used for maneuvering or handling the speculum 10 before, after, or during any procedure. The precise downward angle of the tab 22 may be selected to transition from the plane of the frame 12 to the plane of the zygoma (lateral face or temple). As the tab 22 extends away from the frame 12 it may be reduced in width down to a dimensional width that is used within a procedure. The width at the end of the tab 22 (shown as the two prongs at the end of the tab 22) may be a dimension that is a parameter during a procedure. As an example for eye injections, the width of the end of the tab 22 may be used to assist in determining the standard injection site dimension (approximately 4 mm) posterior to the limbus. In this example, the spacing between the two prongs at the end of the tab 22 may be approximately 4 mm, which removes the need for another tool or device during the procedure. The tab 22 may contain a plurality of ribs to provide a limited slip grip for maneuvering the speculum once in place or during handoffs between an assistant and the provider.

Referring now to FIG. 6, line A-A represents the primary speculum plane which is an imaginary plane in which the top surface 37a of frame 12 is positioned.

Figure 8:
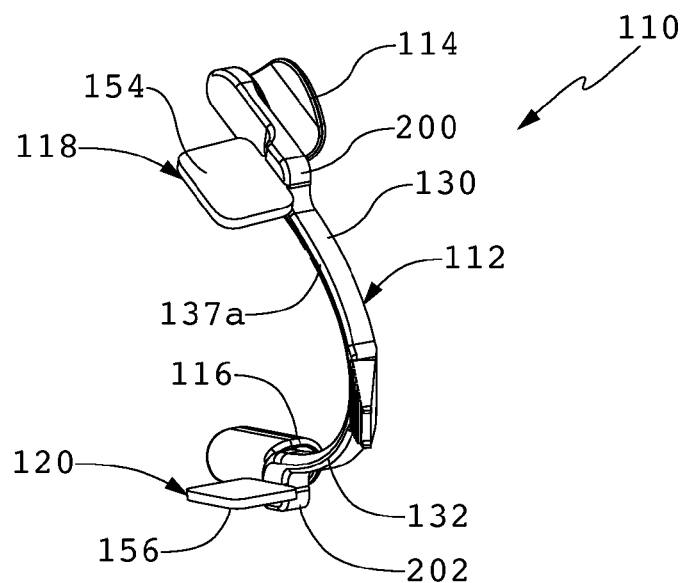
FIG. 8 is a perspective view of an alternative embodiment of a speculum according to the present invention.

Referring now to FIG. 8, this embodiment of a speculum according to the present invention is indicated generally as 110. Speculum 110 is similar to speculum 10, shown in FIGS. 1-7, except that the user manipulation elements are provided as rectangular projections 118 and 120. Each projection 118 and 120 is preferably joined with the respective attachment portion 200 and 202. Each projection 118 and 120 may be fixed within the respective attachment portion 200 and 202 or may be permitted to rotate within the respective attachment portion 200 and 202. Each projection preferably has a rectangular surface 154 and 156 extending upward and away from frame 112. Surfaces 154 and 156 are generally perpendicular to the top 137a of frame 112, although it is within the scope of the invention for the surfaces to be positioned at any angle with respect to the top of the frame. Surfaces 154 and 156 are positioned to receive a force with a direction that is above and parallel to the top of the frame for manipulating arms 130 and 132. Thus, the user can manipulate the surfaces in a position remote from the eye area.

Referring now to FIG. 4, in use, finger 46 is inserted into user manipulation element 18 of speculum 10 and thumb 48 is inserted into user manipulation element 20. User manipulation elements 18 and 20 are squeezed toward each other to reduce the distance between cups 14 and 16. Cup 14 is positioned around upper eyelid 26 and cup 16 is positioned around lower eyelid 28. Interior surfaces 54 and 56 (shown in FIG. 1) of user manipulation elements 18 and 20 are manipulated to move cups 14 and 16 over the desired portion of the eyelids. Tab 22 may also be used to move the frame and position the cups 14 and 16 over the desired portion of the eyelids. Finger 46 and thumb 48 release pressure from surfaces 54 and 56 to increase the distance between cups 14 and 16. Cups 14 and 16 retract upper and lower eyelids 26 and 28 as the distance between the cups increases, thus exposing a desired portion of the eyeball. Thumb 48 pushes user manipulation element 20 and surface 56 (shown in FIG. 1) downward to retract lower eyelid 28 and expose the majority of the anterior side of the inferotemporal quadrant of the eyeball (the lower right portion of the front of the eyeball shown in FIG. 4). After lower eyelid 28 is retracted, a needle (not shown) may be inserted into the eyeball to inject a pharmaceutical into the eyeball. Preferably, the needle is inserted into the inferotemporal region of the pars plana of the eyeball to avoid injury to the lens and retina.

Although the speculum is shown exposing the anterior side of the inferotemporal quadrant, it is within the scope of the invention for the speculum to expose the anterior side of the other three quadrants of the eyeball. For instance, the superotemporal quadrant (the upper right quadrant of the eyeball shown in FIG. 4) may be exposed by pushing user manipulation element 18 and surface 54 upward with finger 46 to retract upper eyelid 26. The inferonasal quadrant (the lower left quadrant of the eyeball shown in FIG. 4) and the superonasal quadrant (the upper left quadrant of the eyeball shown in FIG. 4), may be exposed by first positioning cup 14 around the nasal side of lower eyelid 28 and cup 16 around the nasal side of upper eyelid 26. To expose the superonasal quadrant of the eyeball, thumb 48 pushes user manipulation element 20 and surface 56 upward retracting upper eyelid 26. To expose the inferonasal quadrant of the eyeball, finger 46 pushes user manipulation element 18 and surface 54 downward retracting lower eyelid 28. The speculum may also be used to expose the anterior chamber of the eyeball.

Speculum 110, shown in FIG. 8, operates similarly to speculum 10, described above except that the index finger is positioned adjacent surface 154 and the thumb is positioned adjacent surface 156 for manipulating arms 130 and 132 and frame 112. Speculum 110 otherwise operates in the same manner as speculum 10.

Thus, each of speculums 10 and 110 may retract upper and lower eyelids to expose the anterior side of any portion of an eyeball. The interior surfaces 54 and 56 of user manipulation elements 18 and 20, and surfaces 154 and 156 of projections 118 and 120, enable the speculum to be easily maneuvered to expose any portion of an eyeball. Cups 14, 16, 114 and 116 are sized to contain the eyelashes in order to prevent the eyelashes from contacting the exposed portion of the eyeball, which reduces the likelihood of infection when performing a surgical procedure on the eyeball.

From the foregoing it will be seen that this invention is one well adapted to attain all ends and objectives herein-above set forth, together with the other advantages which are obvious and which are inherent to the invention.

Since many possible embodiments may be made of the invention without departing from the scope thereof, it is to be understood that all matters herein set forth or shown in the accompanying drawings are to be interpreted as illustrative, and not in a limiting sense.

While specific embodiments have been shown and discussed, various modifications may of course be made, and the invention is not limited to the specific forms or arrangement of parts and steps described herein, except insofar as such limitations are included in the following claims. Further, it will be understood that certain features and subcombinations are of utility and may be employed without reference to other features and subcombinations. This is contemplated by and is within the scope of the claims.

I claim:
1. A speculum comprising:
 a first arm beginning at a proximal point and ending at a distal end and having:
  a cup positioned at the distal end;
  an attachment portion positioned on the first arm and proximal to the cup; and a user manipulation element positioned within the attachment portion; and a second arm arising from the proximal point of the first arm and extending to comprise a mirror image of the first arm wherein the first and second arms lie within a primary speculum plane and the user manipulation elements extend away from the primary speculum plane.

2. The speculum of claim 1 wherein:
the user manipulation elements are permitted to rotate relative to the arms.

3. The speculum of claim 1 wherein:
the user manipulation elements are rings.

4. The speculum of claim 1 wherein:
the user manipulation elements are rectangular projections.

5. The speculum of claim 1 further comprising:
a tab extending from the proximal point.

6. The speculum of claim 5 wherein:
the tab is angled towards the user manipulation elements.

7. The speculum of claim 1 wherein:
the cups contain an inside edge which is adapted to fit underneath the marginal edge of the cavity to be dilated.

8. The speculum of claim 7 wherein:
the inside edge comprises a continuous arc.

9. The speculum of claim 1 further comprising:
an opening within the attachment portions;
a compressible prong extending from the user manipulation elements and adapted to fit within the openings; and
a ledge attached to the compressible prongs which prevents the compressible prongs from being removed from the openings.

10. A speculum comprising:
a generally U-shaped frame lying within a primary speculum plane and having a proximal point and pair of distal ends;
a first cup attached to one of the distal ends;
a second cup attached to the remaining distal end;
a first user manipulation element attached to the frame and positioned between the first cup and the proximal point and attached so that the user manipulation element can rotate relative to the frame; and
a second user manipulation element attached to the frame and positioned between the second cup and the proximal point and attached so that the user manipulation element can rotate relative to the frame,
wherein a user's fingers engage with the manipulation elements above the primary speculum plane during use.

11. The speculum of claim 10 wherein:
the user manipulation elements are rings.

12. The speculum of claim 11 further comprising:
a gap within each ring.

13. The speculum of claim 10 further comprising:
a tab extending from the proximal point.

14. The speculum of claim 13 wherein:
the tab is angled away from the cups.

15. The speculum of claim 13 wherein:
the tab decreases in width as it extends away from the proximal point.

16. The speculum of claim 13 further comprising:
a plurality of ribs on the tab.

17. The speculum of claim 10 wherein:
the cups contain an inside edge and an opposing outside edge where the inside edge comprises a continuous arc.

18. A speculum comprising:
a pair of arms lying within a primary speculum plane and joined together at a proximal point, each arm comprising a free first end;
a pair of cups, each cup coupled with a corresponding free first end of one of said arms;
a pair of attachment portions, each one positioned between the cup and the proximal point on each of said arms;
a pair of rings;
a compressible prong extending from each of the rings;
an opening within each of the attachment portions for accepting the compressible prong of each ring such that the compressible prong of each ring extends through the primary speculum plane when inserted into each opening; and
a tab extending from the proximal point.

19. The speculum of claim 18 further comprising:
a gap within each ring.

20. The speculum of claim 18 wherein:
the rings are permitted to rotate within the openings.

* * * * *